United States Patent [19]
Barlow

[11] 4,167,183
[45] Sep. 11, 1979

[54] ANTI-RAPE DEVICE

[76] Inventor: Charles Barlow, 4426 E. 22nd St., Tucson, Ariz. 85711

[21] Appl. No.: 837,904

[22] Filed: Sep. 29, 1977

[51] Int. Cl.² .............................................. A61B 19/00
[52] U.S. Cl. .............................................. 128/138 R
[58] Field of Search ................ 128/132 R, 138, 329, 128/330; 124/1, 20 R

[56] References Cited
U.S. PATENT DOCUMENTS

| | | | |
|---|---|---|---|
| 3,954,103 | 5/1976 | Garcia-Roel et al. | 128/330 |
| 4,016,875 | 4/1977 | Levesque | 128/132 R |
| 4,030,090 | 6/1977 | Vogel | 128/130 |

*Primary Examiner*—Lawrence W. Trapp

*Attorney, Agent, or Firm*—Mason, Kolehmainen, Rathburn & Wyss

[57] ABSTRACT

An anti-rape device adapted to be inserted into the vaginal cavity of a human female, which comprises a base member to which is attached elongated penis penetrating means which projects outwardly toward the mouth of the vaginal cavity when the device is operationally positioned within the vaginal cavity of a human female. The elongated penis penetrating means is surrounded or enveloped by retractable means which serves to prevent the walls of the vaginal cavity from contacting the penis penetrating means and which is adapted to be retracted upon penetration of the vaginal cavity by a male penis to permit penetration of the penis by the penis penetrating means.

6 Claims, 6 Drawing Figures

ANTI-RAPE DEVICE

The present invention relates to an improved anti-rape device and more particularly to a device which is adapted to be inserted into the vaginal cavity of a human female and to be worn by the female as protection against unauthorized entry of a male penis into the vaginal cavity of the wearer. Devices for the same purpose are disclosed in U.S. Pat. No. 4,016,875—Levesque and U.S. Pat. No. 4,030,490—Vogel. However, these prior art devices are not only complicated in structure but are also devoid of any means for positively identifying a female attacker as a rapist.

Accordingly, it is an object of the present invention to provide an improved anti-rape device of the character indicated which can be comfortably worn by a human female and operationally offers a means of identifying a female attacker as a rapist by any member of the medical profession.

It is another object of the invention to provide a device of the character indicated which is simple and economical to construct and easy to use.

The invention, both as to its organization and methods of use and operation, together with further objects and advantages thereof, will best be understood by reference to the specification taken in connection with the accompanying drawings, in which.

Figure 1:
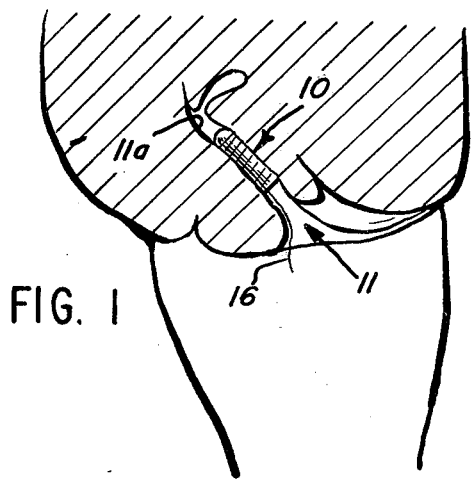
FIG. 1 is a side view of the device illustrating the intended use of the invention.

Referring now to the drawings and more particularly to FIG. 1 thereof, the present improved anti-rape device 10 is there illustrated in its inserted position within the vaginal cavity 11 of a human female. In order to facilitate withdrawal of the device 10 from the cavity 11 and to enhance the comfort to the wearer of the device, the outer walls of the device, which contact the walls 11a defining the vaginal cavity, are preferably coated with an inert lubricating jelly prior to insertion of the device within the cavity 11. More specifically and as best shown in FIGS. 1, 2, 3A and 3B of the drawings, the device 10 comprises a base member 12, penis penetrating means in the form of a slender reed-like element 13 and retractable means in the form of a light easily compressible coil spring 14 which surrounds the reed-like element 13 and serves to isolate the vaginal walls 11a of a wearer from contact with the reed-like element 13. The coil spring 14 is enveloped throughout its length by a flexible plastic cloth tube 15 one end of which is suitably attached to the base member 12 and the other end of which is folded inwardly on itself to surround the free end coil of the coil spring 14. A short length of string 16 is attached to an intermediate coil 14a of the coil spring 14 to facilitate removal of the device 10 from the cavity 11.

Figure 2:
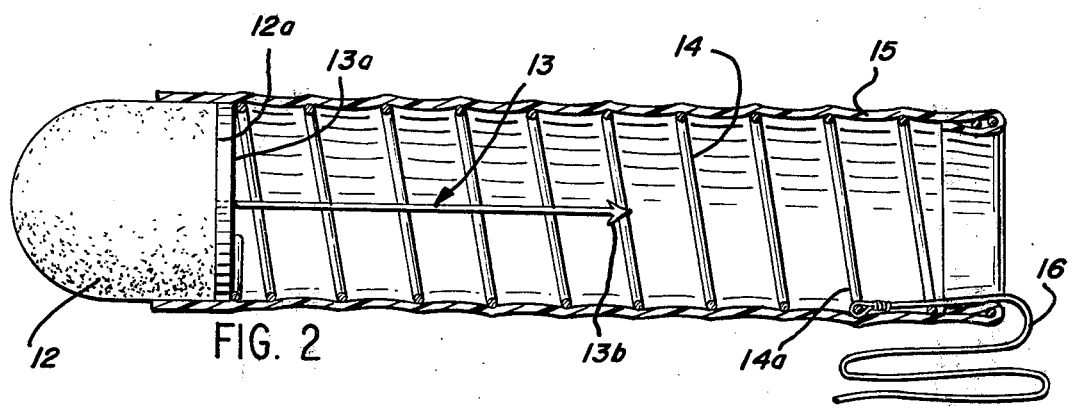
FIG. 2 is a partial sectional view of the device.

More in detail and as best shown in FIG. 2, the base member 12 is preferably formed of a relatively soft plastic material and the reed-like element 13 is provided with an enlarged base end 13a which is adhesively bonded to the end surface 12a of the base member. Alternatively, the enlarged base end 13a of the element 13 may be embedded in the base member 12. At its free or penetrating end the reed-like element 13, which is preferably made of surgical steel, is provided with a pointed harpoon-like tip 13b which prevents withdrawal of the element 13 from an intruding male penis once the penis is impaled on the element 13.

Figure 3A:
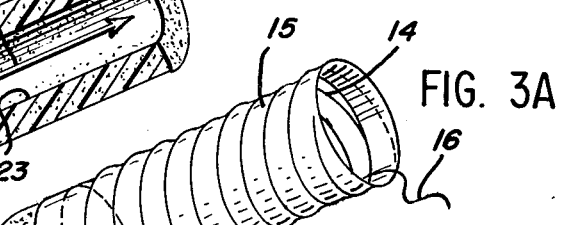
FIG. 3A is a perspective view of the device.
Figure 3B:
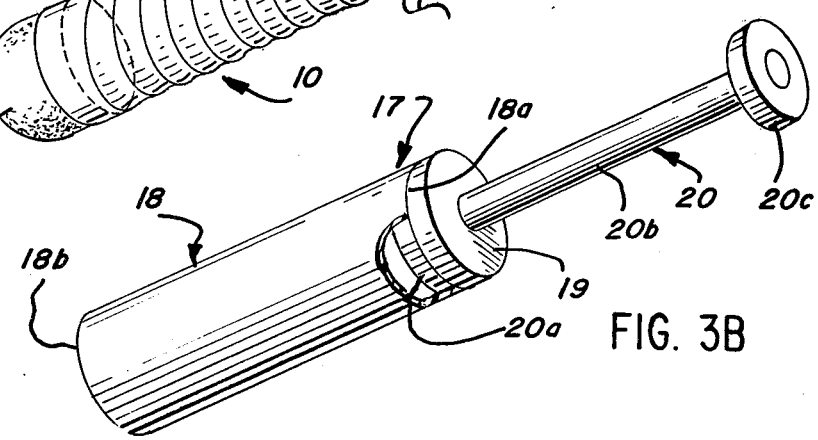
FIG. 3B is a partially broken away perspective view illustrating an applicator device which is usable to emplace the device shown in FIG. 2 within the vaginal cavity of a user.

Referring now to FIG. 3B of the drawings, the applicator device 17 there shown is adapted to be used to insert the anti-rape device 10 in the vaginal cavity 11 of a human female. Briefly, the device 17 comprises a tubular member 18 one end 18a of which is closed by a closure member 19 to which the tube end 18a is fixedly attached to any suitable manner. The other end 18b of the tubular member 18 is open to permit the anti-rape device 10 to be slidably received within the member 18. In order to eject the device 10 from the member 18 an ejecting plunger 20 is provided which comprises an ejecting head 20a disposed within the member 18 and to which is fixedly attached an operating stem 20b which is slidably supported within a central opening provided in the closure member 19. At its operating end the stem 20b is provided with an enlarged head 20c which serves to limit the travel of the head 20a within the tubular member 18.

In order to insert the device 10 in the vaginal cavity 11 of a user, the user simply drops the device 10 in the tubular member 18 with the ejecting plunger 20 in its illustrated fully retracted position and with the pointed end 13b of the element 13 pointing toward the closure member 19. The tubular member 18 is then inserted into the vaginal cavity 11 of the user, following which the ejecting plunger 20 is slowly depressed to withdraw the tubular member 18 from around the device 10 and thus leave the device 10 in operative position within the cavity 11.

In operation, if an intruding penis is attempted to be inserted into the vaginal cavity 11, the retractable spring member 14 is compressed along with its cloth cover 15, permitting the reed-like element to penetrate the intruding penis. Thus the harpoon-like end 13b of the element 13 buries itself in the intruding penis with the result that withdrawal of the penis causes the entire device 10 to be withdrawn from the vaginal cavity 11 with the penis solidly impaled on the element 13. It is expected that medical assistance will normally be required to remove the element 13 from the penis of the female attacker, which course means that the attending physician can readily identify the attacker as a rapist and so inform the appropriate law enforcement agency.

Figure 4:
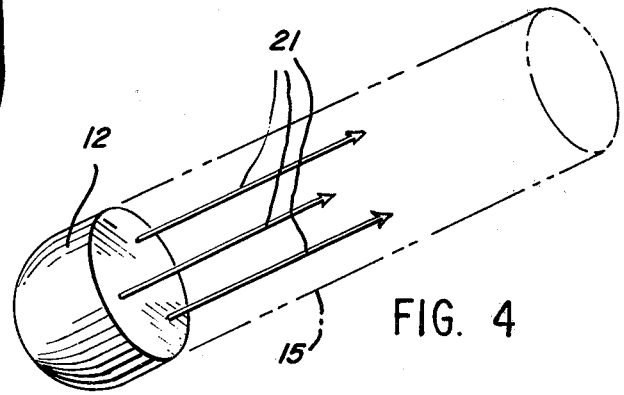
FIG. 4 is a perspective view partially in phantom, showing a modified embodiment of the invention.

In the modified embodiment of the invention illustrated in FIG. 4 of the drawings the penis penetrating means comprises a plurality of harpoon tipped reed-like elements 21 which are suitable mounted on the base member 12 in spaced apart relationship. Otherwise the construction of this modified arrangement is the same as that of the device shown in FIG. 2.

Figure 5:
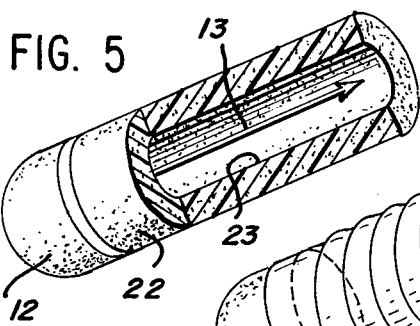
FIG. 5 is a perspective view partially in section illustrating still another embodiment of the invention.

In the modified arrangement illustrated in FIG. 5 of the drawings, the retractable means 22 is formed of a soft, compressible sponge rubber or plastic material which is suitably attached to the base member 12 and is provided with a centrally disposed channel 23 extending throughout the length thereof to receive the harpoon tipped reed-like element 13. This modified structure has the advantage that the use of an applicator device, such as the device 17, is not required in order to insert the device in the vaginal cavity 11 of a user. Specifically, insertion of the device into the cavity may easily be accomplished by finger squeezing the sponge material of the retractable means 22 against the harpoon tipped end of the element 13 and then inserting the device in place within the cavity 11 of the user.

What is claimed as new is:

1. An anti-rape device adapted to be inserted into the vaginal cavity of a human female, comprising a base member, elongated penis penetrating means attached to the base member to project outwardly toward the mouth of the vaginal cavity when the device is operationally positioned within the vaginal cavity of a human female, and retractable means normally surrounding said elongated penis penetrating means to protect the walls of the vaginal cavity from contacting said penis penetrating means, said retractable means being adapted to be retracted upon penetration of the vaginal cavity by a male penis to permit penetration of the penis by said penis penetrating means.

2. A device as claimed in claim 1, wherein said penis penetrating means comprises a slender element which is supported by said base member at one end thereof and is provided with anchoring means at the other free end thereof for anchoring the element in a male penis which penetrates the vaginal cavity of a wearer of the device and is impaled by said slender element.

3. A device as claimed in claim 2, wherein said anchoring means comprises a harpoon-like tip on the free end of said slender element.

4. A device as claimed in claim 1, wherein said retractable means comprises a coil spring enveloping said penis penetrating means.

5. A device as claimed in claim 4, wherein said penis penetrating means comprises a slender element which is supported by said base member at one end thereof and extends at least partially through said coil spring and is provided with anchoring means at the other free end thereof for anchoring the element in a male penis which penetrates the vaginal cavity of a wearer of the device and is impaled by said slender element.

6. A device as claimed in claim 5, wherein said anchoring means comprises a harpoon-like tip on the free end of said slender element.

* * * * *